United States Patent [19]
Stoddard et al.

[11] Patent Number: 5,730,530
[45] Date of Patent: Mar. 24, 1998

[54] AUTOCLAVE RECEPTACLE

[76] Inventors: James T. Stoddard, 1700 Northwood Ave.; Charles D. Stoddard, 1845 Darby Dr., both of Florence, Ala. 35630

[21] Appl. No.: 374,685
[22] PCT Filed: Jun. 28, 1993
[86] PCT No.: PCT/US93/06164
    § 371 Date: Jan. 26, 1995
    § 102(e) Date: Jan. 26, 1995
[87] PCT Pub. No.: WO94/02382
    PCT Pub. Date: Feb. 3, 1994

Related U.S. Application Data

[63] Continuation-in-part of Ser. No. 920,904, Apr. 28, 1992, Pat. No. 5,222,600.

[51] Int. Cl.[6] .......................... B65D 30/04; B65D 33/01
[52] U.S. Cl. .......................... 383/113; 206/439; 383/87; 383/117; 383/122; 493/267
[58] Field of Search .................. 206/45.34, 63.5, 206/370, 438, 439, 484.1; 383/78–86, 86.1, 87, 101, 102, 107, 113, 117, 122; 493/267

[56] References Cited

U.S. PATENT DOCUMENTS

| | | |
|---|---|---|
| 2,177,906 | 10/1939 | Miller . |
| 2,257,517 | 9/1941 | Spotts . |
| 2,709,467 | 5/1955 | Hoeppner ........................ 383/87 |
| 2,999,521 | 9/1961 | Bono et al. . |
| 3,826,296 | 7/1974 | Morris . |
| 3,991,881 | 11/1976 | Augurt ........................... 206/439 |
| 4,010,785 | 3/1977 | Patik ............................. 383/87 |
| 4,427,129 | 1/1984 | Wyslotsky et al. .............. 206/45.34 |
| 4,537,313 | 8/1985 | Workman ....................... 206/545 |
| 5,320,843 | 6/1994 | Raheja et al. ................... 206/438 |

FOREIGN PATENT DOCUMENTS

469028  10/1950  Canada ............................ 383/86

*Primary Examiner*—Jimmy G. Foster
*Attorney, Agent, or Firm*—Mark Clodfelter

[57] ABSTRACT

A receptacle (10) is constructed having first and second broad sides connected along side and bottom edges (12) and (14), respectively. These sides are in turn constructed of an outer layer (28) of flexible, durable fabric material, and in one embodiment, an inner layer (26) of the fabric material. In this embodiment, a barrier material (24) may be placed between the inner and outer layers of at least one of the sides. In a preferred embodiment, a flap closure (20) configured as a cuff (40) extends from one of the sides adjacent opening (18), and folds over opening (18) so as to close the opening.

17 Claims, 7 Drawing Sheets

AUTOCLAVE RECEPTACLE

CROSS REFERENCE TO RELATED APPLICATION

This application is a 371 of PCT/0593/06164, filed Jun. 28, 1993 and a continuation-in-part of U.S. patent application Ser. No. 07/920,904, filed Jul. 28, 1992, now U.S. Pat. No. 5,222,600.

FIELD OF THE INVENTION

This invention relates generally to durable fabric receptacles, and particularly to a receptacle having sides and a closure constructed of a continuous strip of a fabric material, generally with at least one of said sides incorporating barrier material against particulates and liquids.

BACKGROUND OF THE INVENTION

With emergence of AIDS, an insidious immunodeficient disease that occurs in humans and is caused most probably by a retrovirus of simian origin, and commonly acquired by contact with blood and/or blood products from an infected individual, great concern has developed in the medical community over handling and sterilization of contaminated medical instruments. At present, and as is commonly done, instruments used for invasive procedures by surgeons, dentists, nurses, and others of the medical profession are received or collected, typically by an individual who, during the last step of sterilizing the instruments in preparation for their next use, sorts the instruments in accordance with a particular protocol and sterilizes them in an autoclave which may utilize steam, dry heat, or a sterilizing toxic gas such as ethylene oxide. When the instruments are placed in the autoclave, they may be wrapped in a towel, placed in a disposable plastic bag and hermetically sealed, or as is commonly done in hospitals, the instruments may be placed in paper bags or paper tubes constructed for the purpose of autoclaving instruments and simply taped shut using autoclave tape. In the instance where a number of instruments are assembled to form a kit for a particular application, such as a suture kit for repairing lacerations or cuts, the instruments may be packed together in a disposable plastic tray with a hermetically sealed plastic cover, with the tray containing the instruments being processed in an autoclave to effect sterilization of its contents. After the sterilization process is completed, the bags, trays, or other containers containing the instruments are removed from the autoclave, and in the instance where they are to be used immediately, such as in a surgical or dental application, are carried to the site of the procedure. If the instruments are stored for any length of time, they are placed in a relatively secure environment isolated from contaminating materials. When used, the containers are opened, the instruments removed, and the containers discarded.

One of the problems associated with these methods of preparation of instruments for sterilization is that the paper and plastic bags, even if the instruments are wrapped in gauze, are generally not durable enough to withstand the razor sharpness of scalpels and sharpened needle-like instruments, resulting in the bags being cut or punctured. Additionally, in the event the paper bags become wetted, as by condensation of steam in the autoclave, durability of the paper container is greatly decreased. Further, in a non-sterile environment, moisture can permeate the paper containers, carrying contaminants to the interior thereof and rendering instruments therein non-sterile. Further, the use of disposable bags greatly increases the quantity of medical waste and adds to medical costs inasmuch as in addition to the cost of procuring the bags, there is additional cost to dispose of the bags as medical waste. Also, in the event where instruments are wrapped in towels to be sterilized, there is a possibility that they may be wrapped too tight or that too many instruments may be packed together, decreasing effectiveness of the sterilization process. More importantly, while preparing the instruments for sterilization, the non-sterile instruments must be handled in order to place them in the aforementioned containers. Here, there is a distinct danger to the individual involved with the task of sterilizing the instruments of being accidently pricked or cut by a contaminated instrument and possibly acquiring a communicable disease as a result.

Accordingly, it is an object of this invention to provide a method and apparatus that affords greater protection to individuals who handle surgical instruments in the process of sterilizing such instruments while eliminating the necessity of using disposable, non-durable paper and plastic bags during sterilization thereof. Additionally, it is an object of this invention to provide a receptacle for other articles that is protective against dust and moisture.

SUMMARY OF THE INVENTION

A receptacle having first and second opposed sides constructed of a durable fabric material is disclosed. First, second, and third edges of the receptacle are connected, with fourth edges of the sides defining an opening to the receptacle, which is covered by a closure. A layer of particulate and liquid barrier material may be used with at least one of the sides.

DETAILED DESCRIPTION OF THE DRAWINGS

Figures 1, 2, 3, 3A:
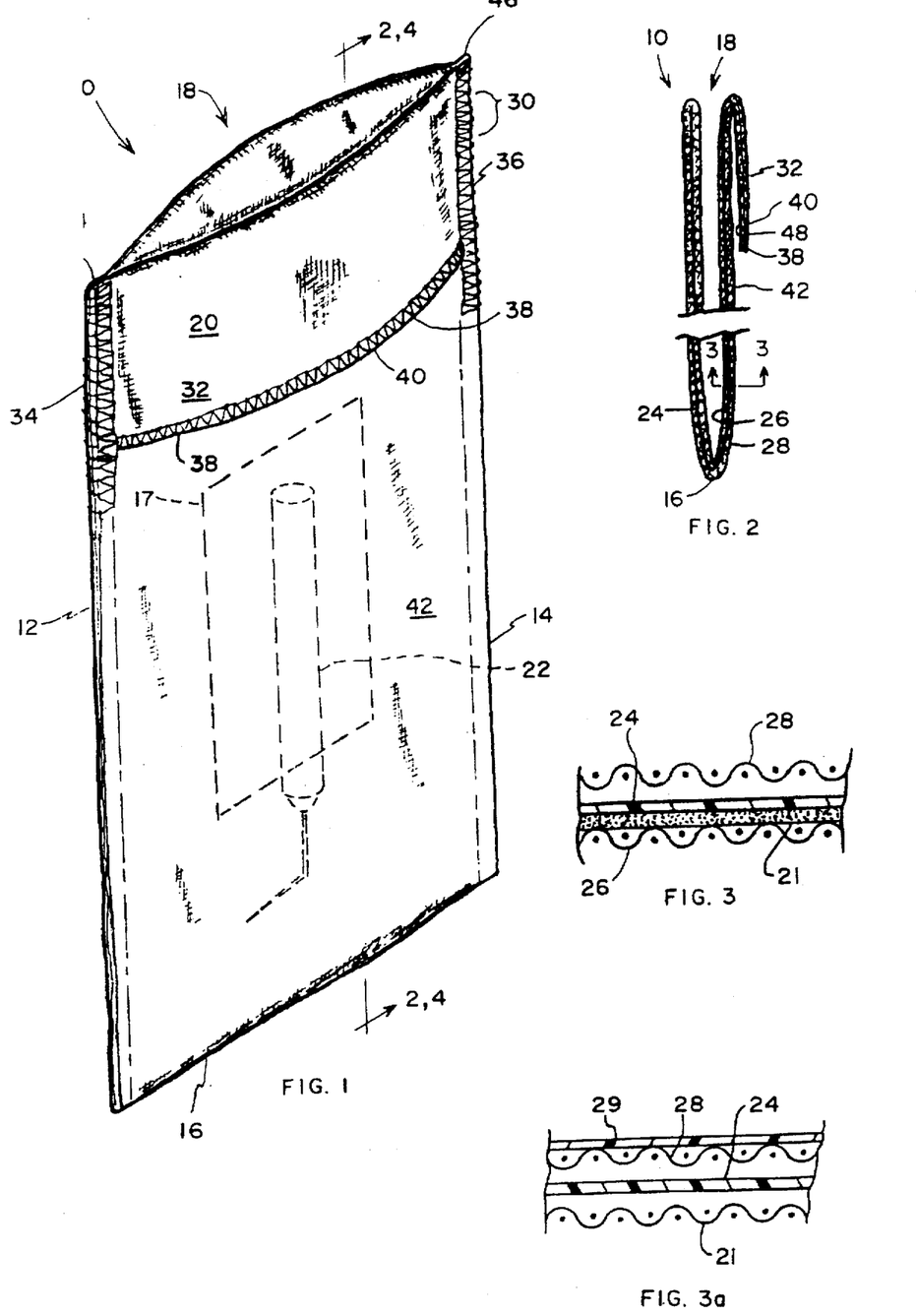
FIG. 1 is a pictorial view of a receptacle of the present invention.
FIG. 2 is a broken sectional view taken along lines 2—2 of FIG. 1.
FIG. 3 is a sectional view of layered construction of the receptacle.
FIG. 3a is a sectional view of layered construction of the receptacle showing a layer of barrier material on an external side of the receptacle.

While a durable, reusable receptacle 10 as shown in FIG. 1 is particularly described in the preferred embodiments of this disclosure, it is to be appreciated that construction and materials of the receptacle may vary without departing from the scope of this invention. As shown, receptacle 20 is basically a flattened pouch or bag structure closed on first, second, and third edges 12, 14, and end 16, respectively, with the fourth edge 18 being open. As such, articles requiring protection of one type or another may be placed in receptacle 10, as illustrated by a dental pick 22 (dashed lines). In addition to medical instruments, a receptacle 10 may be easily adapted for other purposes; for instance by constructing a protective carrier for electronic circuit boards by coating a receptacle 10 of the present invention with a static-electricity dissipating coating.

In a medical application, receptacle 10 may serve as an autoclave receptacle for containing medical instruments during sterilization, and for maintaining sterility over a period of time. Thus far, tests have shown that sterility of a receptacle of the present invention is maintainable up to about 190 days. This sterilization receptacle (FIGS. 1, 2, and 3) is constructed generally of a fabric-enclosed barrier material, such as a pliable plastic film 24 of from about 1 to 5 mils thick, and which may be NYLON (TM), POLYESTER (TM), or any other suitable sheet material having barrier properties such as to block passage of dirt, dust, and microorganisms. Further, the barrier material provides protection against liquids that may wet the fabric and possibly contaminate objects therein. Additionally, the barrier material should be sufficiently rigid to lend form and strength to the receptacle, while generally conforming to the shape of objects placed inside.

As shown in FIG. 3, a plastic sheet material having an adhesive layer 21 which becomes adhesively active with application of heat and pressure may be used, such as a polyester laminate material distributed by CREATIVE IMPRINTS of Atlanta Ga. Otherwise, an adhesive applied, as by a spray apparatus, either to the fabric or barrier material may be used to bond the fabric and barrier material together. This barrier material, when laminated or bonded to an interior layer of fabric 26 of receptacle 10, has been found to provide the necessary qualities as described above, in addition to being puncture resistant. This is significant as some medical instruments have sharpened edges or points which, in the instance of certain sharpened and curved dental picks, may penetrate the inner layer of fabric and become entangled therein. Further, with the inner layer of fabric bonded to the barrier material, small cuts or breaks in the inner layer of fabric do not ravel, as the individual broken threads remain bonded to the plastic layer. This feature is instrumental in maintaining integrity of the receptacles over at least several hundred sterilization cycles. In addition, bonding the inner layer of the receptacle to the barrier material facilitates manufacture of the receptacles by preventing the plastic layer from shifting during cutting and stitching operations.

Alternately, as shown in FIG. 3a, a barrier material may be applied to the exterior of the receptacle as a coating 29, such as found in a printing process commonly known as a "heat transfer" process. This process uses heat and pressure to transfer a thin layer of clear or colored plasticized material over the exterior of the receptacle, which material covering sides of the receptacle and serving as the barrier material. In this instance, printed matter such as that indicating contents of the receptacle and/or their use, etc. would be incorporated in a layer of the plasticized material applied to an exterior region of the receptacle in the aforementioned "heat transfer" process.

In the instance where medical instruments are sterilized in receptacles of the present invention, the receptacle may be preferably constructed of a fabric known as BIOGUARD (TM), and which is manufactured by Burlington Industries Inc, (TM). This fabric is permanently impregnated with a substance having disinfectant properties against most Gram positive and Gram negative bacteria. More generally, the fabric material may be a typical surgical muslin material, which has a thread count of about 160 threads per inch. Otherwise, any durable fabric material may be used.

In a basic receptacle 10, side edges 12 and 14 are constructed of open seams sewed closed, preferably by a serge-type stitch 30 (FIG. 1) having about 10 stitches per inch, for preventing the fabric edges from ravelling. Additionally, in the serging process, a small excess of barrier material and fabric is removed along the edges just prior to being serged, providing cleanly severed edges of fabric and barrier material which are immediately sewed. Additionally, by removing a small amount of fabric and barrier material, it is assured that the barrier material extends through the stitched area to the edges of the receptacle. Closed end 16 is a seam formed by simply folding the material. A sealer, such as a silicone sealant which forms an impervious film, or a sealing tape, may be applied to or incorporated with the stitched regions for sealing such stitched regions, making them impervious to microorganisms, liquids and other contaminants.

If desired, aligned openings 17 (dashed lines in FIG. 1) may be constructed in the layer or layers of fabric, and with a transparent plastic film 24 used as the barrier material, a window in the receptacle is defined through which contents of the receptacle may be examined.

Figure 13:
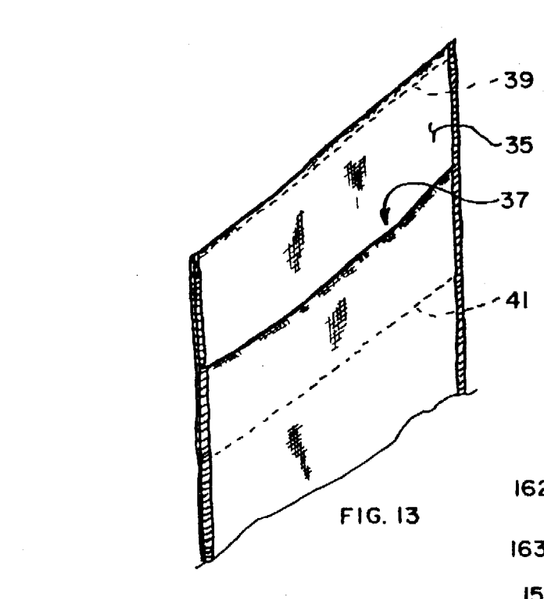
FIG. 13 is a broken away view of a receptacle having a flap closure.
Figure 13A:
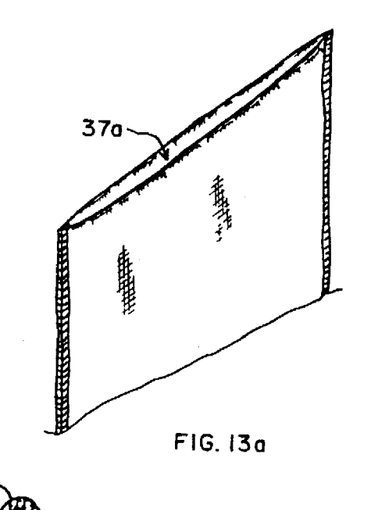
FIG. 13a is a cut-away pictorial view of an alternate embodiment of a receptacle of the present invention.
Figure 13B:
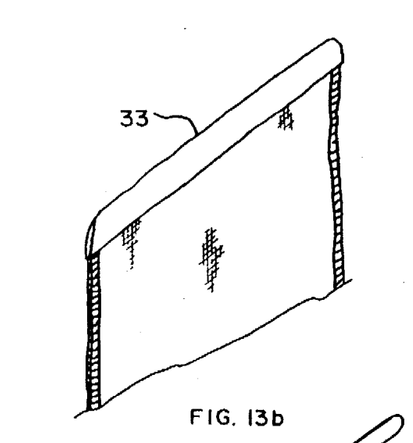
FIG. 13b is a pictorial view of the receptacle of FIG. 13a wherein the opening thereof is sealed with tape.

In a simplest embodiment of a closure of a receptacle of the present invention, and as shown in FIGS. 13a and 13b, a receptacle is constructed having an opening 37a which is sealed by autoclave tape 33. In this embodiment, the autoclave tape serves as the closure.

For sealing opening 18 of receptacle 10 against microbial and other particulate challenges, and in a preferred closure, a closure 20 is constructed as shown in FIG. 2 as having a flap 32 of fabric material formed as a folded extension continuous with front inner and outer layers 26 and 28 of fabric, respectively, with edges 34 and 36 (FIG. 1) of flap 32 being sewn integral with edges 12 and 14, respectively, of the receptacle. During fabrication, end 38 of flap 32 is serged as described to prevent the muslin from ravelling, and folded downward such that a cuff 40 is formed against front side 42 of the receptacle after being sewn along the edges.

Figure 4:
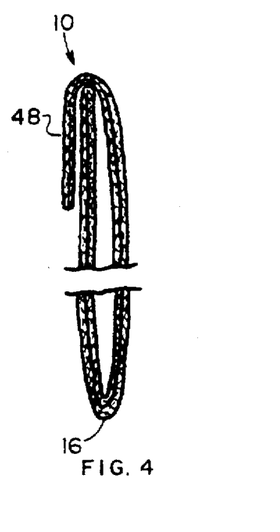
FIG. 4 is a broken, sectional view taken along lines 4—4 of FIG. 1 illustrating a closure of the receptacle in a closed position.
Figure 5:
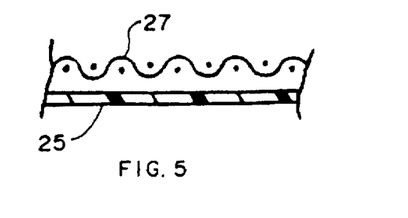
FIG. 5 is a cut-away view illustrating an alternate layered construction of the present invention.

Cuff 40 is operated to close receptacle 10 by inverting upper corners 44 and 46 downward and through the interior of the cuff, and inverting and folding the cuff over opening 18 such that inner side 48 of cuff 40 is exposed on an opposite side of receptacle 10, as shown in FIG. 4. This type of closure for opening 18, when used with autoclave tape over the interface between cuff 40 and the receptacle, has been found to effect a seal such that the receptacle is secure against microbial breaches. Where it is intended the receptacle and sterilized instruments therein are to be stored for a period of time, the autoclave tape, which may have a dye that changes color after undergoing the autoclave process, may be placed over the interface between cuff 40 and the receptacle prior to sterilization to indicate that contents of the receptacle have been sterilized. Further, when used, the autoclave tape provides a convenient medium upon which a date the sterilization occurs may be placed.

Security of this receptacle, when used with autoclave tape as described, is evidenced by microbial challenge test run #93047 performed by PHARMACUTICAL SYSTEMS INC. of 102 Terrace, Mundelein, Ill., 60060. In this test, 5 unused receptacles and 5 receptacles having undergone a minimum of 250 sterilization cycles were sterilized and then challenged by an aerosol containing about $3 \times 10^5$/ml spores of *bacillus subtillis*, with the result that all the receptacles remained sterile. Further, since the cuff closure, when inverted over the opening of the receptacle, holds the opening closed and covers the opening, it is believed that autoclave tape is unnecessary to cover or seal the interface between the inverted cuff and the exterior of the receptacle.

Alternately, as shown in FIG. 13, the receptacle may be constructed simply having a flap 35 positioned adjacent the opening 37, and which is folded over the opening and secured with other types of closures, which may include VELCRO (TM), buttons or zippers or other fasteners positioned along regions 39 and 41 of the receptacle. As stated, autoclave tape may be used to cover the interface between the flap and receptacle after the flap is folded over opening 37, although it is one object of this invention to provide a sterilization receptacle that avoids the use of disposable materials and the increased cost associated therewith.

Figure 14:
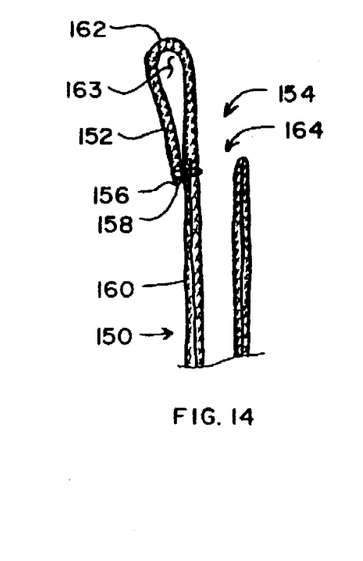
FIG. 14 is a partial, cut-away view of construction of a rollable closure of a receptacle of the present invention.
Figure 14A:
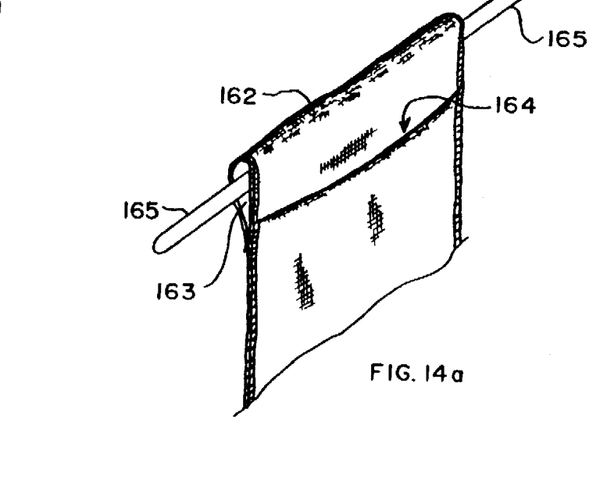
FIG. 14a is is a partial pictorial view of the rolled closure showing a securing strip in place.
Figures 14B, 14C:
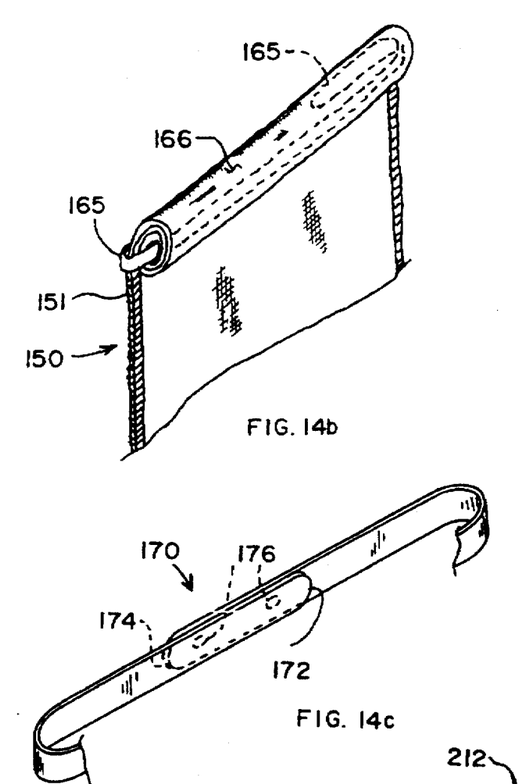
FIG. 14b is a view of the rolled closure after the closure is rolled and secured.
FIG. 14c is a partial pictorial view of another embodiment of a securing strip.

One particular embodiment of a closure is seen in FIGS. 14–14b. Here, a receptacle 150 is constructed having a flap portion 152 extending above a level of opening 154 of the receptacle, which flap being folded so that ends 156 and 158 of a strip of fabric are brought together and sewed to an exterior region 160 of the receptacle, This forms a looped region 162 having a tubular region 163 therein. A length 165 (FIG. 14a) of flexible, malleable metal or other material is inserted through tubular region 163 such that ends thereof extend about equally on both sides side of receptacle 150, and flap 152 is rolled forward to enclose opening 164 (FIG. 14b). The extending portions of strip 165 are then bent to engage a side 151 of receptacle 150 opposite opening 164 to hold the rolled portion 166 in place over opening 164.

Alternately, a strip 170 (FIG. 14c) may be constructed of a length so that ends 172 and 174 overlap when folded as described, with male/female fittings 176 positioned on respective ends of the overlapping regions. In use, after the looped region 162 is rolled to form roll 166, the extending portions of strip 170 are folded behind the receptacle as described, and the male/female portions snapped together, holding rolled portion 166 in place over opening 164.

Figure 15:
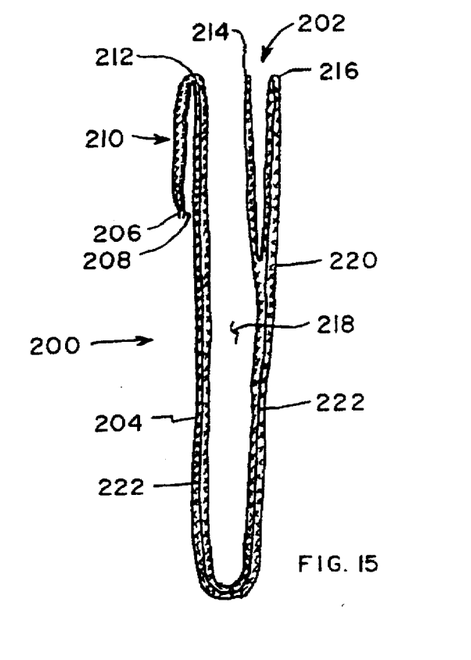
FIG. 15 is a cut-away view of a receptacle having a pocket formed from an inner layer of fabric material.
Figure 15A:
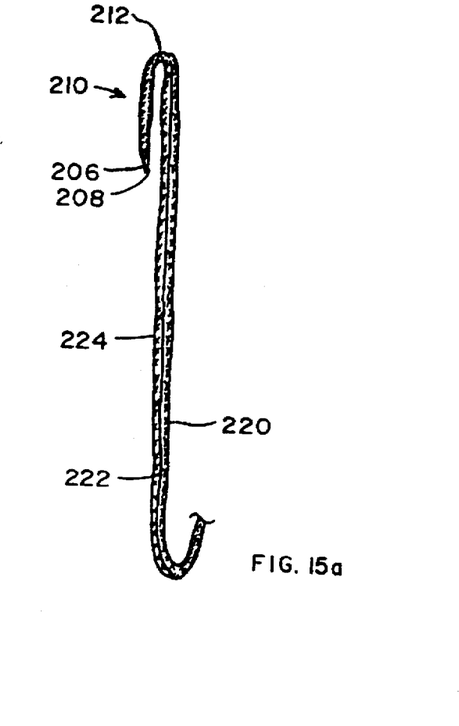
FIG. 15a is a partial, cut-away view of a receptacle having a barrier material in only one of broad sides thereof.

As shown in FIG. 15, a strip of barrier material 222 may be incorporated in both outer sides of the receptacle, or as shown in FIG. 15a, the barrier material 222 may be incorporated in only one side 224 of the receptacle. This is desirable where instruments such as dental handpieces, which are constructed of components susceptible to rust and corrosion, are sterilized in the receptacle. After sterilization, residual moisture in and on the handpiece evaporates, with the water vapor passing through a side 220 of the receptacle constructed only of fabric material. Additionally, with the barrier material associated with a single side of the receptacle having the flap thereon, as shown in FIG. 15a, the closed, sterilized receptacle containing sterilized instruments may be placed on a non-sterile surface with the side having the barrier material thereagainst and the flap facing up, preventing external contaminants that may be present on the non-sterile surface from penetrating the fabric, rendering the instruments non-sterile.

In the instance where instruments not likely to rust or corrode are to be stored for a period of time, both sides of the receptacle would be constructed having the barrier material so as to provide maximum protection against infiltration of liquids, microorganisms and other particulate material.

Figure 9:
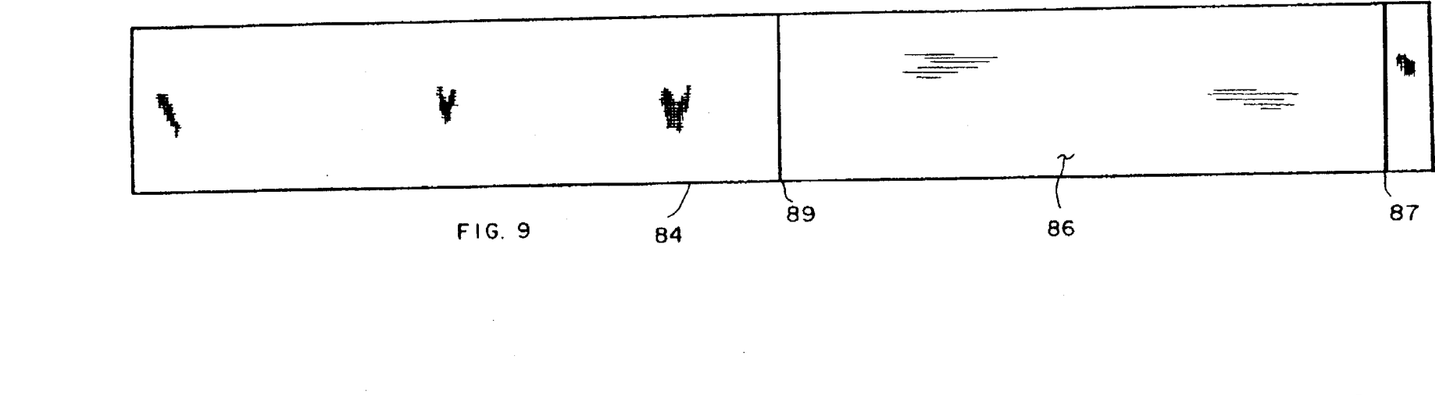
FIG. 9 is a planar view of a strip of fabric and barrier material positioned thereon and from which a receptacle of the present invention is constructed.
Figure 10:
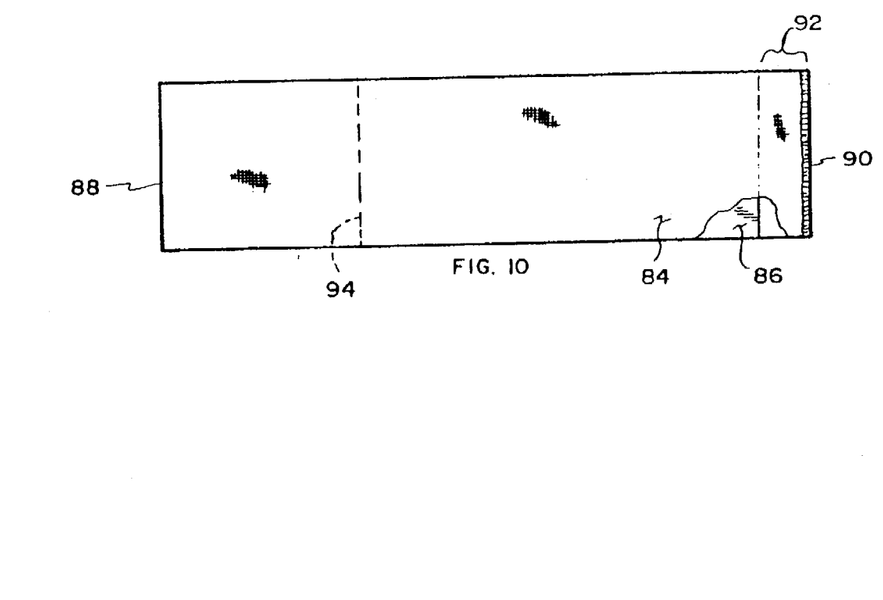
FIG. 10 is a planar view of the strip of fabric once folded to enclose the barrier material.
Figure 11:
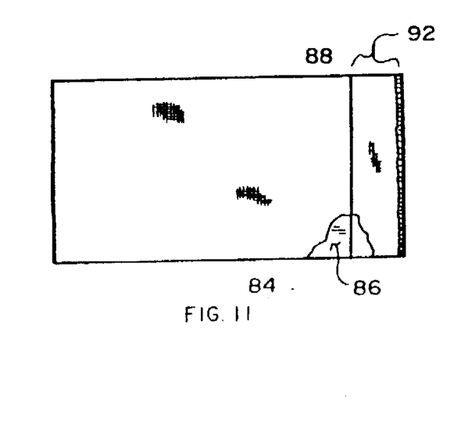
FIG. 11 is a planar view of the strip of fabric and barrier material folded to form sides of the receptacle.
Figure 12:
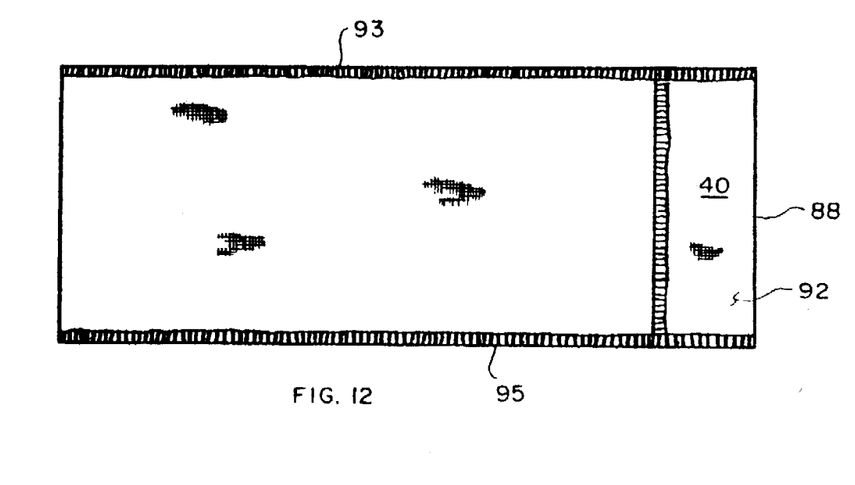
FIG. 12 is a planar view of a completed receptacle.

For constructing a receptacle as shown in FIG. 1, and referring to FIG. 9, a strip of fabric 84 is cut having a width about 1.27 cm wider than a width of the finished receptacle, and of a length generally 4 times that of the finished receptacle plus twice the length of cuff 40. A strip 86 of barrier material is cut having a like width as strip 84, but only about twice as long as the finished receptacle. Where only one side of the receptacle is to incorporate the barrier material, the strip of barrier material is only about a quarter as long as the fabric strip. The longer barrier strip 86 is positioned as shown in FIG. 9 to cover strip 84 from a point 87 to a point 89 located at a midpoint of strip 84. In the instance where the barrier strip is laminated to the fabric, as by the aforementioned laminate material distributed by CREATIVE IMPRINTS (TM), the adhesive side is placed adjacent the fabric and heat and pressure applied. Otherwise, a coating of adhesive may be applied to the fabric or barrier material, such as a spray adhesive, and the fabric and barrier material pressed together until bonding occurs. Strip 84 is then folded, as shown in FIG. 10, positioning barrier material strip 86 between the folded sections of fabric strip 84. A folded end region 88 is formed in the fabric strip, with barrier material 86 abutted against this folded end region 88. At an opposite end 90 of the folded fabric strip, the ends of strip 84 are aligned and serged together, forming an end of a cuff region 92 (dotted lines) at end 90. Plastic strip 86 generally does not extend into cuff region 92 because it would render the cuff inordinately stiff. This folded strip is again folded as shown in FIG. 11 so that barrier material strip 86 is folded in half, and the partially completed receptacle is turned over. Cuff region 92 is then folded to cover an adjacent side as shown in FIG. 12 to form cuff 40. Edges 93 and 95 are then serged, closing edges of the receptacle and securing edges of cuff 40 along edges of the receptacle. Serging at the corners of the receptacle is backtacked to reinforce the corners and prevent the stitching from ravelling. If desired, the aforementioned silicone sealer may then be applied to exterior stitches to fully seal the receptacle. Alternately, after the receptacle is completed, an exterior barrier material may be applied by the aforementioned "heat transfer" or other printing process, as shown by layer 29 of FIG. 3a.

Figure 6:
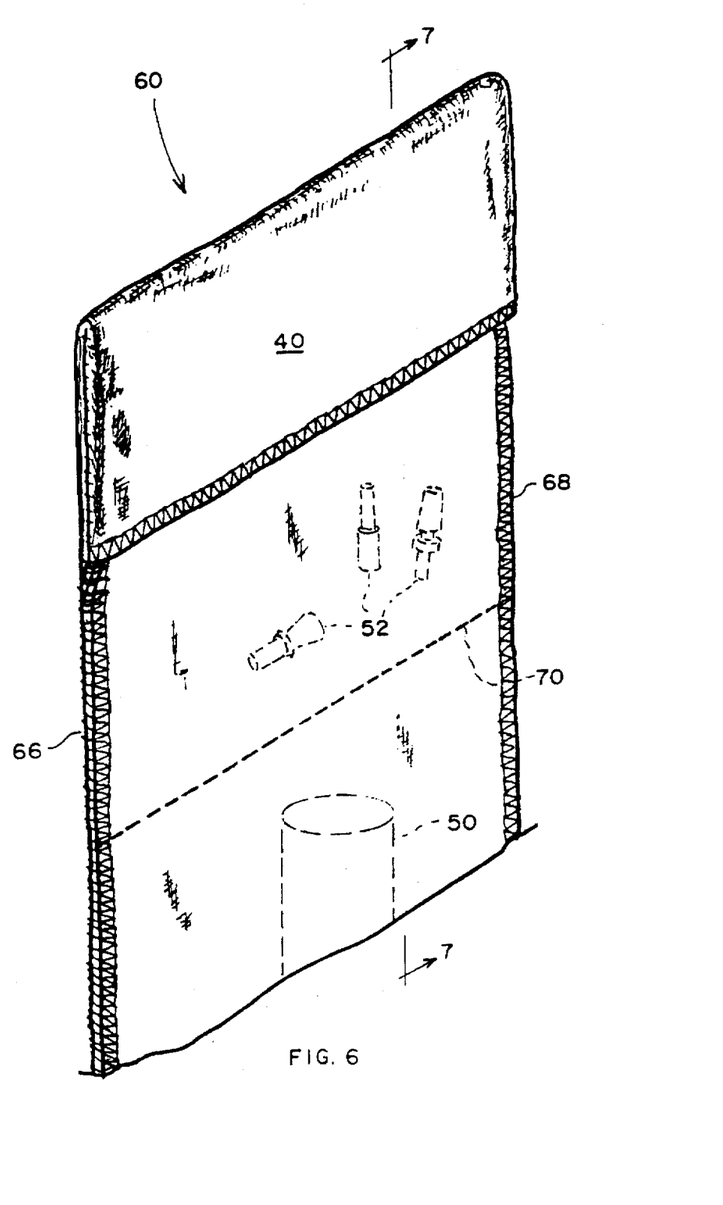
FIG. 6 is a partially cut-away view of an alternate embodiment of the invention.
Figure 7:
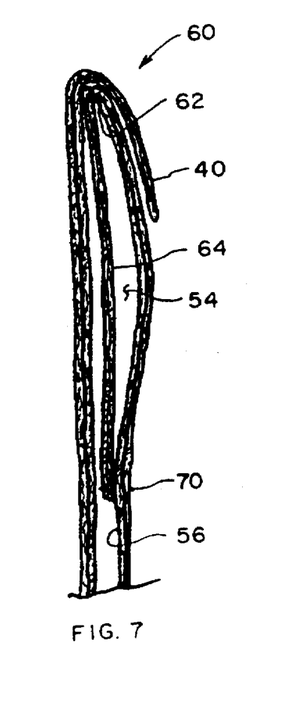
FIG. 7 is a sectional view partially cut away and taken along lines 7—7 of FIG. 6.

In the instance where several instruments or implements are used together during a procedure, such as a dental handpiece 50 (FIG. 6) having a chuck for coupling a number of differing drills, burrs, cleaning pads and other implements 52 to the handpiece, FIGS. 6 and 7 illustrate an embodiment of the present invention wherein a pocket 54 is constructed on an inner side 56 of a receptacle 60 constructed in accordance with the foregoing. An upper opening 62 to the pocket is formed on an inside region of receptacle 60 between a strip 64 of fabric and interior side 56 of the receptacle opposite from a side of the receptacle having cuff 40 thereon. Here, as with flap 30, strip 64 is sewn integral with receptacle 60 along sides 66 and 68 thereof, and is sewed in a transverse direction along a bottom side to side 56, as illustrated by stitched line 70, defining the pocket 54 where small implements or instruments 52 may be placed for sterilization along with the handpiece. Pocket 54 may be constructed of any size as necessary, and may extend partially along inner side 56, or extend the full length of side 56. Additionally, a plurality of pockets (not shown) may be constructed in a single receptacle such that each pocket may contain a plurality of identical burrs, drills, or the like, for sterilization. When cuff 40 is folded and inverted as described, opening 62 and the opening for receptacle 60 are covered by cuff 40, as shown in FIGS. 6 and 7.

Where an interior pocket is to be added, a strip of surgical muslin twice a length of the pocket and the same width as strips 84 and 86 (FIG. 9) is folded in half and the two ends serged together. The folded region of this strip is aligned with end 88 of the side of strip 84 shown in FIG. 10 and stitched at the serged end to the strip of FIG. 10 at about dotted line 94, forming an interior pocket as shown in FIG. 7. Significantly, this produces a pocket having folded edges at the opening thereof, so that there is no stitching at these edges to become entangled with instruments placed in the receptacle or pocket.

Figure 8:
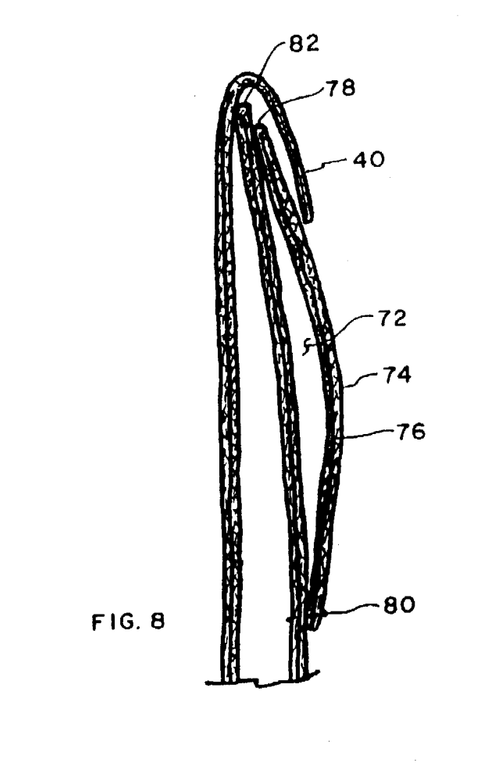
FIG. 8 is cut-away view of an alternate embodiment of the invention as shown in FIGS. 6 and 7.

For positioning the pocket on an exterior region of the receptacle so that certain medical instruments do not become entangled in the stitching of the opening of the receptacle or the stitching of the pocket, FIG. 8 illustrates an embodiment of the receptacle wherein an exterior pocket 72 is formed from a strip 74 of fabric. Strip 74 is folded to enclose a plastic sheet 76, forming a fold 78, with ends of the strip 74 and plastic sheet 76 therebetween sewed to the receptacle at 80 and along sides to the receptacle as described above. Significantly, the folded region 78 is not aligned with the top of folded end 82 of the receptacle, but is downwardly offset about 0.635 cm, allowing easier access to pocket 72. Constructed as such, folded region 78 and folded end 82 of the receptacle define the opening in the receptacle and the opening of the pocket, precluding a possibility of an instrument becoming entangled in stitching. As shown in FIGS. 6, 7, and 8, cuff 40 is operated to close openings of the pocket and receptacle.

In another embodiment of a receptacle having a pocket or pockets, and as shown in FIG. 15, a receptacle 200 having a pocket 202 is constructed of a contiguous strip of fabric 204 having ends 206 and 208 serged together to form an end of flap or cuff 210. As such, the openings to pocket 202 and interior 218 of the receptacle are bordered by folded regions of fabric 212, 214, and 216, eliminating the possibility of an instrument becoming entangled in stitching or a hemmed or stitched region as it is being inserted or removed from the receptacle or the pocket. Pocket 202 is formed by folding and doubling the interior portion of the strip of fabric so that fold 214 forms one edge of the opening of pocket 202, with the other edge of the opening formed by folded edge 216 of an exterior wall 220 of the receptacle. As such, the receptacle has folded edges adjacent the openings to the receptacle and pocket, with no sewed edges or seams that instruments may become entangled in. Further, the bottom of the receptacle comprises a folded edge which is advantageous to prevent entanglement of instruments, and which further is more resistant to penetration by needle-like instruments than a sewed edge or seam.

Figure 16:
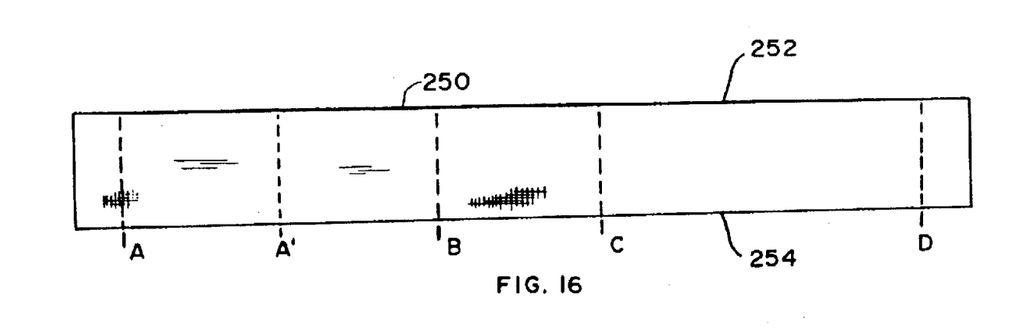
FIG. 16 is a view of a strip of fabric from which a receptacle having a pocket is made, and showing layout of components of the receptacle prior to the strip being folded.

For constructing a receptacle as shown in FIGS. 15 and 15a, and referring to FIG. 16, a continuous strip of fabric 250 is cut of a length double the length of the cuff, pocket, and body of the receptacle, in addition to about 1.27 cm in width and length, for providing a slight excess of fabric and barrier material. This excess is removed as described in the serging process, providing a cleanly cut and serged edge, and further insures that the barrier material extends through the stitching. Here, the body of the receptacle extends between points A–B and C–D, the pocket extends from points B–C, and the flap closure extends from points A and D to respective ends of strip 250. The sheet of barrier material is of a like width as strip 250, and in the instance where both sides of the receptacle are to be protected thereby, extends from point A to point B. Where the barrier material is to be between layers of only one side of the receptacle, the barrier material is positioned to extend from point A' to points A or B, depending on which side of the receptacle the barrier material is associated. As stated in the foregoing, the strip of barrier material may be first adhesively secured to the strip of fabric by a heat activated adhesive, a spray adhesive, or any other type of suitable adhesive material that secures the barrier material to the fabric. This prevents the barrier material from moving out of position during the folding and sewing processes, a convenience in constructing the receptacles. Additionally, with the barrier material laminated or otherwise attached to a side of the interior layer of fabric, the ends of sharpened, hook-like dental probes are prevented from puncturing the inner layer of fabric and becoming entangled therein.

Figure 17:
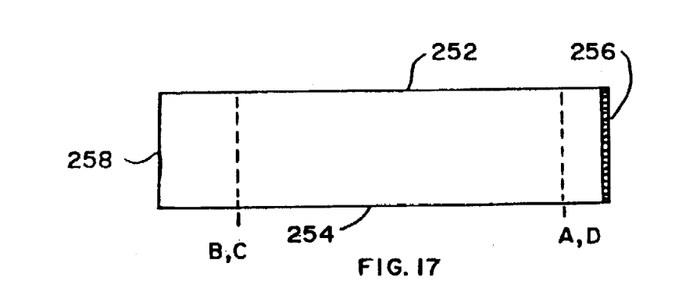
FIG. 17 is a view of the strip of fabric after being folded once.
Figure 18:
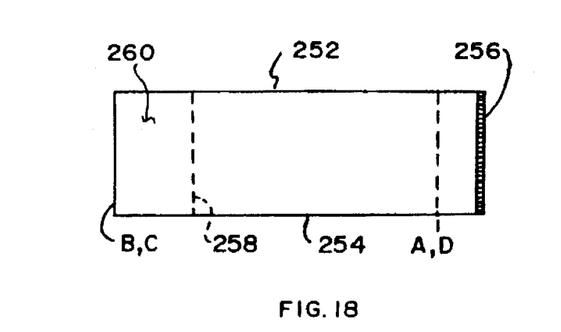
FIG. 18 is a view showing how a pocket is formed in a receptacle of FIGS. 16 and 17.

After the barrier material is secured to or otherwise positioned on the fabric, as between points A and B, strip 250 is folded in half to bring the ends together, with these ends being serged to form end 256 (FIG. 17) of the flap and a folded end 258. Folded end 258 is then inverted inward between the folded layers of fabric, forming pocket 260, as shown in FIG. 18. End B, C, is then folded to point A, D, and sides 252 and 254 are serged and backtacked as described, closing the receptacle on three edges and leaving the fourth edge open at the juncture of B,C and A,D. In the instance where a cuff closure is to be formed, the serged, flap end 256 is folded over an exterior adjacent side prior to serging sides 252 and 254.

Figure 19:
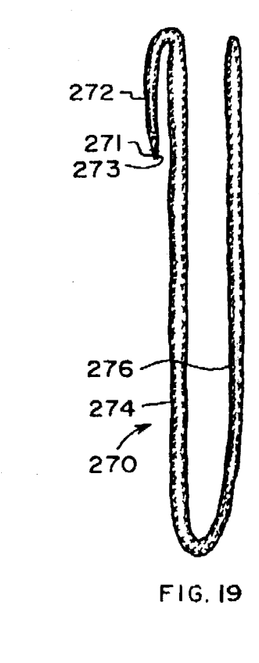
FIG. 19 is a cut-away view of a receptacle constructed of fabric and having a flap closure.

In yet another embodiment of a receptacle of the present invention, FIG. 19 shows a receptacle 270 constructed of a fabric strip as described in the foregoing, but without the barrier material layer. Here, the strip of fabric has ends 271 and 273 stitched together at flap 272, with the strip folded as described to form exterior fabric layer 274 and inner fabric layer 276 of opposed sides of the receptacle. If desired, inner side 276 may be folded to form a pocket (not shown) as described in the foregoing.

Having thus described our invention and the manner of its use, it is apparent that incidental changes may be made thereto without departing from the scope of the following appended claims, wherein we claim:

1. A durable, protective receptacle comprising:

a first side having first, second, third and fourth edges and including at least two layers of a flexible, durable fabric material, said first side being of a vapor permeable character, a second side having first, second, third, and fourth edges and including at least two layers of said flexible, durable fabric material, barrier means including a liquid and microorganism barrier associated with one of said first and second sides, for blocking entrance into said receptacle of liquids and microorganisms through said one of said first and second sides, said first and second sides being in opposed relation, with said first, second, and third edges of said sides being directly attached to each other in terms of their numerically referenced edges, said fourth edges being unconnected to define an opening in said receptacle, and one of said fourth edges constructed as a closure contiguous with said two layers of said fabric material of that said side, said closure extending at least the length of said opening, for completely covering said opening.

2. A receptacle as set forth in claim 1 wherein said layers of fabric material are formed by folding a single strip of said fabric material such that said first and second sides each comprises an inner layer and an outer layer of said fabric material, with a first folded, seamless region defining a lower said edge of said receptacle opposite said opening, and a second folded, seamless region defining a said fourth edge opposed from said closure.

3. A receptacle as set forth in claim 2 wherein said closure is configured as a flap extending from a one of said first and second sides, and being foldable to enclose said opening.

4. A receptacle as set forth in claim 3 wherein said flap is folded over an exterior region of a said side from which said flap extends, and edges of said flap sewed to said edges of said sides adjacent said opening, forming a cuff closure invertible over said opening.

5. A receptacle as set forth in claim 1 comprising a pocket in an interior of said receptacle.

6. A receptacle as set forth in claim 5 wherein said pocket is formed by folding said inner layer of said fabric material of one of said sides so that a folded, seamless edge of said last named inner layer of fabric material defines an opening of said pocket.

7. A receptacle as set forth in claim 1 wherein said barrier means is positioned between inner and outer layers of said fabric material of said second side.

8. A receptacle as set forth in claim 1 wherein said barrier means is adhesively bonded to at least one of said layers of fabric material.

9. A receptacle as set forth in claim 8 wherein said barrier means is bonded to said inner layer of fabric.

10. A receptacle as set forth in claim 1 wherein said barrier means is applied as a coating to at least one exterior side of said receptacle.

11. A method for constructing a reusable sterilization receptacle comprising the steps of:

(1) forming a contiguous strip of fabric having opposed ends and capable of withstanding repeated sterilization, (2) folding said strip to align said opposed ends at one end and form a first folded region at an opposite end, (3) sewing said opposed ends together to form a folded strip having said first folded region at a first end and sewed said opposite ends at a second end, (4) folding said folded strip to bring said first end to a point on said folded strip near said second end, forming first and second sides of said receptacle, said second end extending beyond said first end to form a closure flap, (5) sewing together opposed edges of said first and second sides, forming a receptacle having sewed edges, said sides each having an inner layer of fabric and an outer layer of fabric.

12. A method as set forth in claim 11 further comprising the step of positioning a layer of particulate and liquid barrier material between said inner layer of fabric and said outer layer of fabric of at least one of said sides.

13. A method as set forth in claim 12 further comprising the steps of:

(1) folding said closure flap over said outer layer of fabric, forming a folded region adjacent said opening, (2) attaching sides of said flap to said sewed edges of said receptacle, forming a cuff closure.

14. A method as set forth in claim 11 further comprising the step of folding said inner layer of one of said sides to form a pocket between said inner layer and said outer layer of said last - named side.

15. A durable, protective receptacle comprising:

a first side having first, second, third, and fourth edges and constructed of at least two layers of a flexible, durable fabric material, a second side having first, second, third, and fourth edges and constructed of at least two layers of said flexible, durable fabric material, with at least one of said first and second sides being of a vapor permeable character, said first and second sides being in opposed relation, with said first, second, and third edges of said sides being attached to each other in terms of their numerically referenced edges, said fourth edges being unconnected to define an opening in said receptacle, and said layers of fabric material formed by folding a single strip of said fabric such that said first and second sides each comprises an inner layer and an outer layer of said fabric, with a first, folded seamless region defining a lower edge of said receptacle opposite said opening, and a second, folded seamless region defining a fourth edge opposed from said closure, and one of said fourth edges constructed as a closure contiguous with said two layers of said fabric material of that said side, said closure extending at least the length of said opening, for completely covering said opening.

16. A receptacle as set forth in claim 15 wherein said closure is configured as a flap extending from a one of said first and second sides, for covering said opening.

17. A receptacle as set forth in claim 16 wherein said flap is folded over an exterior region of said side from which said flap extends and edges of said flap sewed to said edges of said sides adjacent said opening, forming a cuff closure invertible over said opening.

* * * * *